(12) United States Patent
Bolk et al.

(10) Patent No.: US 6,452,190 B1
(45) Date of Patent: Sep. 17, 2002

(54) RADIATION DETECTOR PROVIDED WITH AN ABSORPTION CHAMBER AND A PLURALITY OF AVALANCHE CHAMBERS

(75) Inventors: Hendrik Johannes Jan Bolk, Bornerbroek (NL); Klaus Bethke, Almelo (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 34 days.

(21) Appl. No.: 09/621,523

(22) Filed: Jul. 21, 2000

(30) Foreign Application Priority Data

Jul. 23, 1999 (EP) ............................................. 99202444

(51) Int. Cl.[7] .................................................. G01T 1/18
(52) U.S. Cl. ...................... 250/374; 250/375; 250/385.1
(58) Field of Search ................................ 250/374, 375, 250/385.1, 385.2, 389; 313/93

(56) References Cited

U.S. PATENT DOCUMENTS 3,952,197 A    4/1976   Samson ...................... 250/382
4,289,967 A  * 9/1981   Hanson ....................... 250/385
4,359,661 A  * 11/1982  Mitrofanov .................. 313/93

\* cited by examiner

*Primary Examiner*—Seungsook Ham
*Assistant Examiner*—Timothy Moran

(57) ABSTRACT

In order to obtain suitable absorption of the radiation to be detected in the detector gas of a radiation detector, in particular an X-ray detector, the detector is constructed in such a way that the radiation enters the detector parallel to the counting wire, thus offering an absorption path having any desired length. According to the invention, a number of avalanche chambers 50 is arranged adjacent the absorption chamber 46, said avalanche chambers having a comparatively small cross-section. The avalanche chambers are provided with grids 54 in such a way that charge multiplication by the grid voltage can occur only in the avalanche chamber. Due to the comparatively small cross-section of the avalanche chambers, broadening of the current impulses to be detected is prevented. Moreover, the comparatively long absorption chamber offers good radiation absorption and the presence of several avalanche chambers enables a favourable detection rate.

6 Claims, 2 Drawing Sheets

RADIATION DETECTOR PROVIDED WITH AN ABSORPTION CHAMBER AND A PLURALITY OF AVALANCHE CHAMBERS

FIELD OF THE INVENTION

The invention relates to an apparatus for radiation analysis by means of analyzing ionizing radiation, including a radiation detector for detecting the analyzing radiation, which detector includes:

a gas-filled absorption chamber for absorbing the radiation to be detected, which absorption chamber is provided with an entrance window which is formed in a wall of the absorption chamber and is transparent to the radiation to be detected, and at least one counting wire which is arranged in the gas atmosphere, the surface of the entrance window being oriented transversely of the longitudinal direction of the counting wire.

The invention also relates to a radiation detector for use in such an apparatus.

A radiation detector for use in such an apparatus is described in U.S. Pat. No. 3,952,197. The radiation detector described therein includes a gas-filled, elongate chamber, the wall of which constitutes a first electrode. A rod-shaped or wire-shaped second electrode is arranged in a slit-shaped cut-out in the wall in such a manner that it extends parallel to the longitudinal direction of said chamber. A voltage difference exists between the two electrodes, so that a very inhomogeneous electrical field is present in the elongate chamber. The elongate chamber is closed at both its ends by end plates which extend transversely of the longitudinal direction and in which there is provided an entrance window which is permeable to the radiation to be detected.

DESCRIPTION OF PRIOR ART

A radiation detector for use in such an apparatus is described in U.S. Pat. No. 3,952,197. The radiation detector described therein includes a gas-filled, elongate chamber, the wall of which constitutes a first electrode. A rod-shaped or wire-shaped second electrode is arranged in a slit-shaped cut-out in the wall in such a manner that it extends parallel to the longitudinal direction of said chamber. A voltage difference exists between the two electrodes, so that a very inhomogeneous electrical field is present in the elongate chamber. The elongate chamber is closed at both its ends by end plates which extend transversely of the longitudinal direction and in which there is provided an entrance window which is permeable to the radiation to be detected.

In this known radiation detector the ion current to be detected is not amplified in the radiation detector itself. Consequently, for a given radiation intensity the current to be measured is very low or a very high intensity is required.

In radiation detectors of the kind generally known from prior art the problem imposed by an inadequate detection current is solved by producing an avalanche effect, i.e. the particles released upon ionization are accelerated by the electrical field, prior to collision with another gas particle, in such a manner that such a collision produces a new ionization; this process is repeated many times with the particles released by the new ionizations. The avalanche of released particles ultimately reaches the counting wire in which the large number of particles produces a current impulse which is much larger than that produced by a single particle.

Radiation detectors utilizing the avalanche effect, however, have the drawback that the shape of the current impulse is dependent on the location where the ionization, i.e. the beginning of the avalanche, occurs. This phenomenon is due to the fact that the incident X-ray quanta in such radiation detector require a long path through the gas so as to make the probability of ionization high enough for adequate X-ray detection. This means that ionizations occur both close to the counting wire as well as at a comparatively long distance therefrom. An ionization in the gas atmosphere of the detector causes a cloud of electrons whose size is dependent on the energy, i.e. the wavelength, of the X-rays to be detected. Such an ionization-induced cloud travels to the counting wire under the influence of the electrical field in the vicinity of this wire. While traveling to the counting wire the electrons of said cloud are driven apart from one another by mutual electrical repulsion, so that not only gas amplification of the current impulse occurs but also widening of this impulse. Consequently, ionization close to the counting wire produces a sharp impulse whereas, due to said repulsion, an ionization remote from the counting wire causes broadening of the impulse. Because the charge content of the impulse remains the same, the impulse is then also flattened proportionally. Consequently, it may occur that two wide impulses in rapid succession are not distinguished from one another but interpreted as a single impulse of higher energy by the processing electronics, thus leading to incorrect interpretation of the measurements. This problem can be circumvented by inhibiting the detection of a second impulse within a given period of time after a first detected impulse; this given period of time must then be chosen to be equal to the longest possible impulse duration. However, this makes the detector much slower and the duration of measurements will be prolonged proportionally.

SUMMARY OF THE INVENTION

It is an object of the invention to provide a radiation detector of the kind set forth which offers impulses of comparatively high current intensity without the counting speed of the radiation detector being degraded.

To this end, the apparatus for radiation analysis according to the invention is characterized in that the radiation detector is also provided with at least two avalanche chambers which adjoin the absorption chamber, are in atmospheric contact therewith and are intended to produce an avalanche of released charged particles, each of said avalanche chambers being provided with:

a counting wire which is present in the gas atmosphere, a grid which is present in the gas atmosphere and is arranged around the counting wire, the counting wires of said avalanche chambers extending substantially parallel to one another.

Because the surface of the entrance window is oriented transversely of the longitudinal direction of the counting wire, the radiation to be detected is incident substantially parallel to the counting wire in the absorption chamber. The absorption chamber can be constructed so as to have an arbitrary length within broad limits (i.e. the dimension in the direction parallel to the counting wire, so parallel to the incident radiation). Consequently, the absorption of the incident radiation can be proportionally high. The distance between the ionization and the counting wire may then be approximately constant and small, irrespective of the distance between the entrance window and the location of the ionization. The grids of the avalanche chambers are electrically adjusted relative to the absorption chamber in such a manner that an electron cloud formed in the absorption chamber will travel in the direction of the counting wires without the electrons in this cloud causing an avalanche of ionizations in the absorption chamber. Because of the small distance between each ionization and the grid, the electron cloud will hardly be dispersed during this short travel, so that no pulse broadening will be induced in this space. When the electron cloud enters the space between the grid and the counting wires (i.e. the avalanche chamber), it causes an avalanche of ionizations. This is due to the fact that the counting wires in the avalanche chambers are electrically adjusted relative to the grids in such a manner that an adequately strong electrical field is present in the avalanche chamber. Thus, for all electrons entering the avalanche chamber the avalanche commences at substantially the same distance from the counting wire. Because of the design of the avalanche chamber, this distance can be chosen so as to be sufficiently small to prevent broadening of the current impulse to be detected, so that the impulse duration is always short and hence the counting speed may be high.

Because several avalanche chambers are provided, the count rate of the detector may be higher than in the case of only one avalanche chamber. This increase is due to the fact that successive ionizations generally take place in different locations within the absorption chamber, so that the associated electron clouds will also travel to different avalanche chambers. A current impulse makes one avalanche chamber temporarily not accessible for a next impulse (the "idle time"), but another avalanche chamber can deal with an impulse. The effect of the idle time on the count rate of the detector is thus strongly reduced and may even become negligibly small when a sufficiently large number of avalanche chambers is used. Furthermore, because of the chosen construction of an absorption chamber, being separate from the avalanche chambers, the suspension of the counting wires may be such that the avalanche field generated in the avalanche chambers by these wires has an appearance which is not dependent on the location in the longitudinal direction where the electron enters the avalanche chamber. Consequently, this location does not influence the shape of the current impulse to be detected, so that the measuring result cannot be incorrectly interpreted.

Two types of gas-filled radiation detectors can be distinguished: so-called flow detectors and sealed detectors. The former type is used notably in the case of longwave X-rays. Because this type of radiation can be readily absorbed in an X-ray window, a very thin entrance window is used, often being a window made of a synthetic foil. Because such windows readily transmit the detector gas, gas is continuously supplied; this explains the name of these detectors. The latter type is used notably for shortwave X-rays and does not lose gas and hence is referred to as "sealed". It is to be noted that the invention can be used for both types of radiation detector.

The grid in an embodiment of the invention consists of grid wires which extend substantially parallel to the counting wire. This construction also results in an avalanche field which extends uniformly in the longitudinal direction of the counting wire and also enables a robust, comparatively vibration-insensitive suspension of the grid wires. Moreover, a desired cross-sectional shape can be readily imparted to the avalanche chambers bounded by the grid wires.

The avalanche chambers in a further embodiment of the invention directly adjoin one another. If the avalanche chambers were not to adjoin one another, areas in which the electrical field strength is substantially equal to zero would occur in the absorption chamber, so that the electron cloud released by the ionization would not travel in the direction of an avalanche chamber and hence would not be detected. By taking this step it can be ensured that the electron cloud formed in the absorption chamber due to ionization will always arrive in an avalanche chamber and hence will be detected. The probability of detection is thus significantly enhanced.

The avalanche chambers and the absorption chamber in a further embodiment of the invention constitute a contiguous stack. It is thus achieved that all electrons produced by ionization in the absorption chamber always reach an avalanche chamber, the dimensions of the detector nevertheless remaining limited. This can be achieved, for example by imparting a rectangular or square cross-section to the chambers. As a result of such a compact stacking, the individual avalanche chambers may have limited dimensions, offering the described advantages concerning the shape of the current impulse to be detected, a large volume being obtained nevertheless for the avalanche space. The uniformity of the avalanche field extending in the longitudinal direction of the counting wire is not affected by the square shape of the cross-section of the avalanche chambers. The rotational symmetry of the avalanche field, however, is slightly influenced by said, for example square shape, so that an electron entering at a corner of the square traverses a field other than an electron entering halfway the side of the square. However, the effect of this phenomenon is negligibly small for all practical purposes, because mainly the electrical field in the direct vicinity of the counting wire is of importance. The latter part of the field is hardly influenced by a square shape of the avalanche chamber.

BRIEF DESCRIPTION OF THE DRAWING

The invention will be described in detail hereinafter with reference to the Figures in which corresponding reference numerals denote corresponding elements. Therein.

DETAILED DESCRIPTION OF THE PREFERRED EMBODIMENTS

Figure 1:
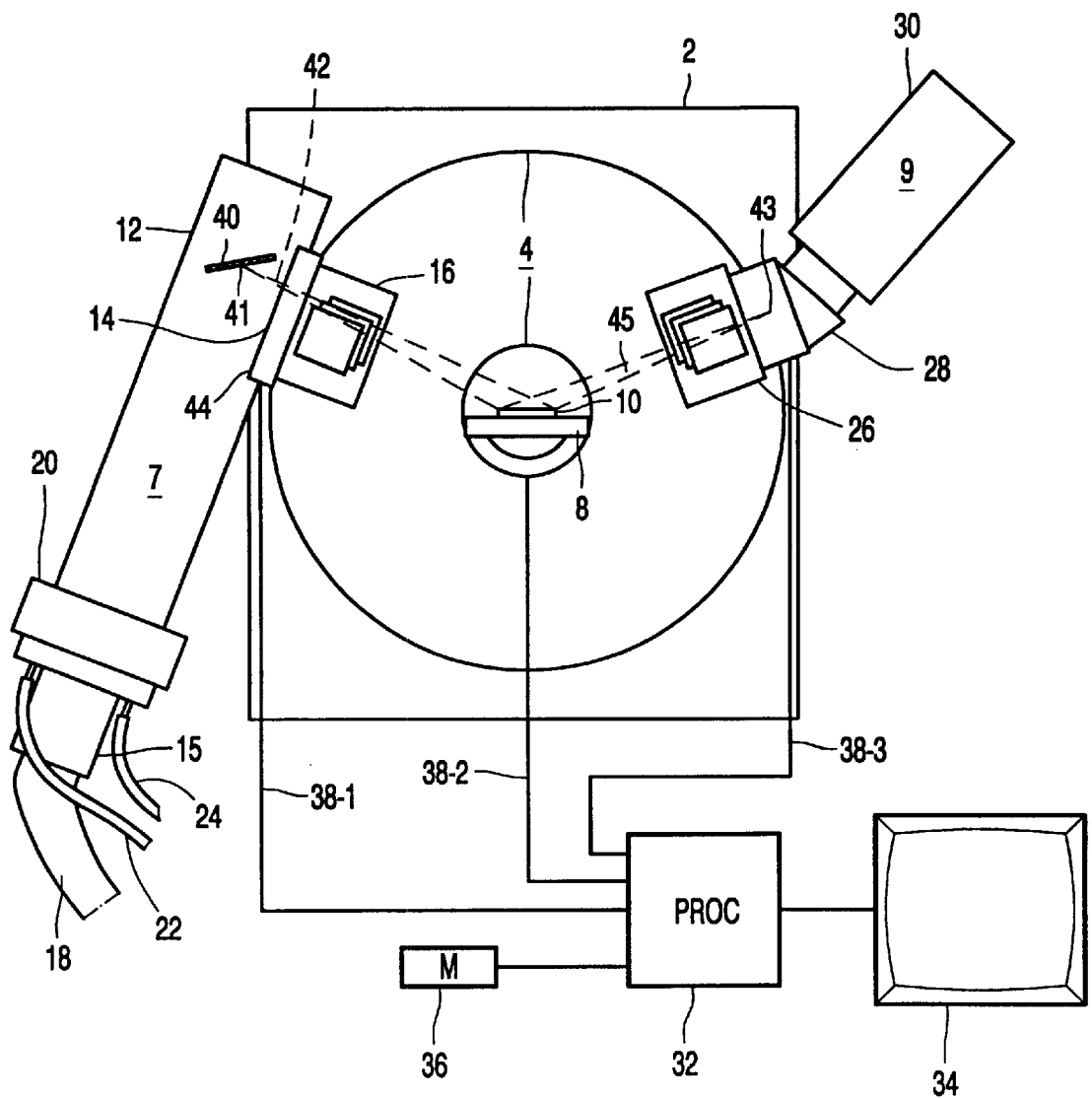
FIG. 1 is a general view of a known X-ray analysis apparatus in which the invention can be used.

FIG. 1 is a general view of a known X-ray analysis apparatus in which the invention can be used;

The invention will be described in detail hereinafter on the basis of an embodiment in which apparatus for radiation analysis is formed by an X-ray analysis apparatus, more particularly, an X-ray diffraction apparatus. Therein, the analyzing ionizing radiation are X-rays. However, it is to be noted that the invention can be used in other radiation analysis apparatus in which the analyzing radiation has the form of ionizing radiation. FIG. 1 is a diagrammatic representation of an X-ray diffraction apparatus which is known per se. Therein, a goniometer 4 is mounted on a frame 2. The goniometer may be provided with an angular encoder for measuring the angular rotation of the X-ray source mounted thereon and of the detector device 9 which is also mounted thereon. Moreover, the goniometer is provided with a sample carrier 8 on which a sample 10 is arranged. In those cases where measurement of the angular rotation of the sample is important, an angular encoder may be provided on the sample carrier. The X-ray source 7 includes a holder 12 for an X-ray tube which is not shown in this Figure and is secured in the holder by way of a fixing ring 20. The X-ray tube is provided with a high-voltage connector 15 for applying the high voltage and the filament current for the X-ray tube via a high-voltage cable 18. The supply and discharge ducts 22 and 24 for the cooling water of the X-ray tube are provided on the same side of the X-ray tube. The tube holder 12 also includes an exit window for X-rays 44 and a unit 16 for parallelization of the X-ray beam (a Soller slit unit). The plates of the Soller slit unit 16 extend parallel to the plane of drawing so that the radiation beam produced by the X-ray source 7 irradiates the sample 10 with a beam which diverges in the plane of drawing. The detector device 9 consists of a holder 26 for a Soller slit unit, a holder 28 for a monochromator crystal, and a detector 30. The plates of the Soller slit unit in the holder 26 also extend parallel to the plane of drawing. If the X-ray source and the detector are both rotatable about the sample, it is not necessary for the sample to be mounted so as to be rotatable. However, it is alternatively possible to mount the X-ray source so as to be stationary as this may sometimes be necessary in the case of heavy and voluminous X-ray sources. In that case the sample holder and the detector should both be rotatable.

The X-ray diffraction apparatus as shown in FIG. 1 also includes a processing device for processing the various measured data. This processing device consists of a central processing unit 32 with a memory unit 36 and a monitor 34 for the presentation of the various data and for the display of the measured and calculated result. The X-ray source 7, the detector device 9 and the sample carrier 8, mounted on the goniometer 4, are all provided with a unit (not shown) for determining the angular position of the relevant element relative to the scaled graduation of the goniometer. A signal representing this angular position is applied to the central processing unit 32 via connection leads 38-1, 38-2 and 38-3.

FIG. 1 shows a so-called Bragg-Brentano arrangement, which means that the X-rays emanating from a single point are again focused at one point after reflection by the sample 10, provided that the surface of the sample is tangent to a circle extending through the point of origin and the focal point. The sample 10 is irradiated by means of X-rays originating from the X-ray source 7. An anode 40, which forms part of the X-ray tube that is not shown in this Figure, is diagrammatically represented. The X-rays are generated in a customary manner in the anode 40 by exposing the anode to high-energetic electrons. Thus, X-rays 42 are generated in the anode, which X-rays emerge via the X-ray window 44. In the arrangement shown in FIG. 1 said point wherefrom the X-rays emanate is not formed by a single point, but by a line focus 41 on the anode, which line focus extends perpendicularly to the plane of drawing. Said focal point is formed by the point of union 43 of the beam 45 emanating from the sample at the area of the entrance of the detector 30. Consequently, this arrangement has a focusing effect only in the plane of drawing.

Figure 2:
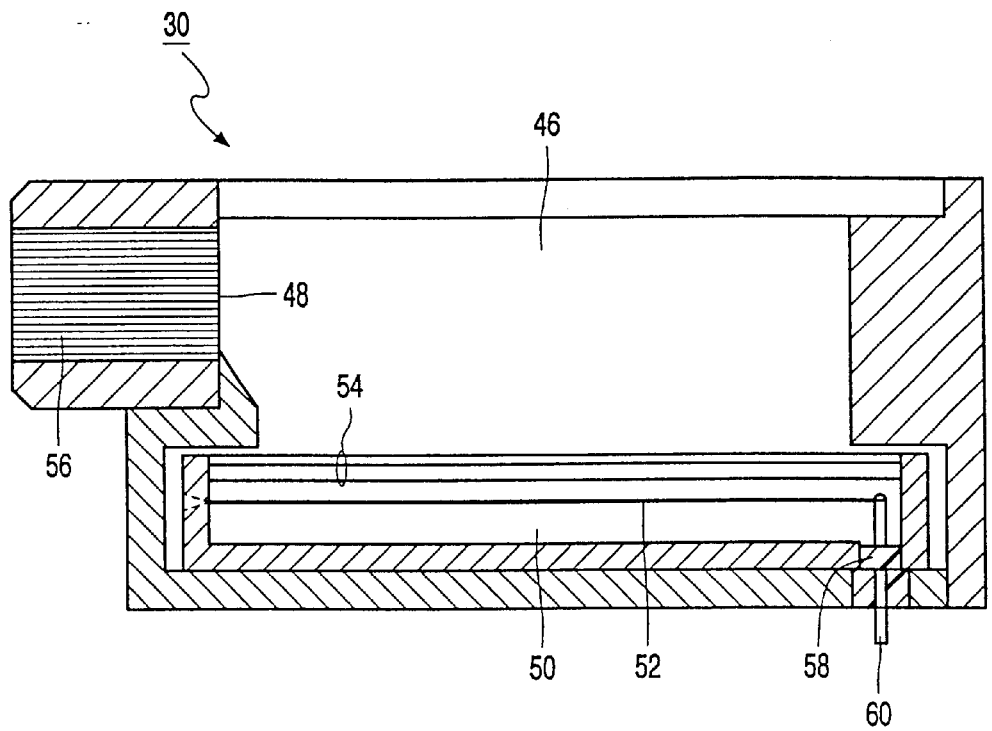
FIG. 2 is a sectional view in the longitudinal direction of a radiation detector according to the invention.

FIG. 2 is a sectional view in the longitudinal direction of a radiation detector according to the invention. The detector 30 consists essentially of two chambers, i.e. an absorption chamber 46 and an avalanche chamber 50. The radiation to be detected enters the detector 30 via a detector collimator 56 which consists of a stack of parallel plates of an X-ray absorbing material wherebetween slits are situated in the present example. The collimator removes radiation which does not originate from the analysis crystal or does not have the correct direction. The collimator 56 bears against the X-ray transparent entrance window 48 which seals the interior of the detector from the environment in a gastight manner. The absorption chamber 46 is filled with a gas which can be ionized by the incident X-rays, for example argon or xenon; these gases have an ionization energy of the order of magnitude of from 25 eV to 30 eV.

The avalanche chamber 50 directly adjoins the absorption chamber 46. The avalanche chamber is in atmospheric contact with the absorption chamber, i.e. charged particles released in the absorption chamber 46 can freely travel to the avalanche chamber 50 through the gas filling of the two chambers. The avalanche chamber 50 is separated from the absorption chamber 46 by a grid which consists of a number of parallel grid wires 54 in the present embodiment. These grid wires partly enclose a counting wire 52 as is shown in greater detail in FIG. 3.

The housing of the absorption chamber 46 is at ground potential. The grid wires 54 are adjusted to a voltage of the order of magnitude of between +200 V and +500 V relative to the housing, for example +300 V, whereas the counting wire is adjusted to a voltage of the order of magnitude of, for example 2 kV. The voltage is applied to the counting wire 52 by a power supply source (not shown) via a conductor 60 which is provided in an insulating passage 58.

An X-ray quantum entering the absorption chamber 46 can cause a number of ionizations of the gas in this chamber, an electron and a positively charged ion then being formed each time. The number of ionizations per X-ray quantum is dependent on the wavelength of the radiation, and hence on the energy of the quantum. Therefore, the detector is a so-called energy-dispersive detector, which means that the detector outputs a signal which is proportional to the energy of the detected X-ray quanta. Under the influence of the electrical field formed by the grid wires 54, the electrons formed by the ionization travel through the absorption chamber in a direction which is oriented substantially perpendicularly to the grid wires. For an arbitrarily long absorption path (i.e. the distance between the ionization and the entrance window 48), in comparison with the absorption path the distance to be traveled by the electrons formed during the ionization is small for all electrons, irrespective of the length of the absorption path.

As soon as the electron arrives at the area of the grid wires 54, its motion is determined by the electrical field produced by the voltage difference between the grid wires 54 and the counting wire 52. The latter field is much stronger than the field in the absorption chamber 46, because the distance between the grid wires 54 and the counting wire 52 is smaller than the distance between the grid wires 54 and the wall of the absorption chamber 46, and because the voltage between the grid wires 54 and the counting wire 52 is much higher than that between the grid wires 54 and the wall of the chamber 46. Due to the strong field in the avalanche chamber 50, an electron entering said chamber causes new ionizations time and again; this avalanche effect results in a multiplication of charge carriers of the order of magnitude of from $10^3$ to $10^4$ times. The cloud of electrons caused by the avalanche effect ultimately is incident on the counting wire 52 in which it causes a current impulse which is strong enough so as to be readily detected.

Regardless of the location in the longitudinal direction of the detector (i.e. in the direction of the grid wires 54 and the counting wire 52) where the ionization of a gas particle takes place, the avalanche formation will always take place in substantially the same way, because the ionizing electron always enters the avalanche chamber in the same vicinity, viewed electrically, where it has to travel the same distance to the counting wire 52. This is achieved by the method of mounting of the counting wire 52 and the grid wires 54. One end of the counting wire 52 is connected to an insulator whereas its other end is connected to the input of the signal processing electronic circuitry (not shown). Both ends of the grid wires are conductively connected to the required grid voltage. FIG. 2 shows that these connection locations are shielded from the absorption chamber 46, so that these connection locations are not visible from the locations where the ionizations take place. Thus, any field distortions caused by this connection will not be experienced by the avalanche-forming electrons. Disregarding statistical fluctuations which are inherent of the ionization and avalanche process, all ionizations by X-ray quanta of the same energy will then yield the same current impulses in the counting wire.

Figure 3:
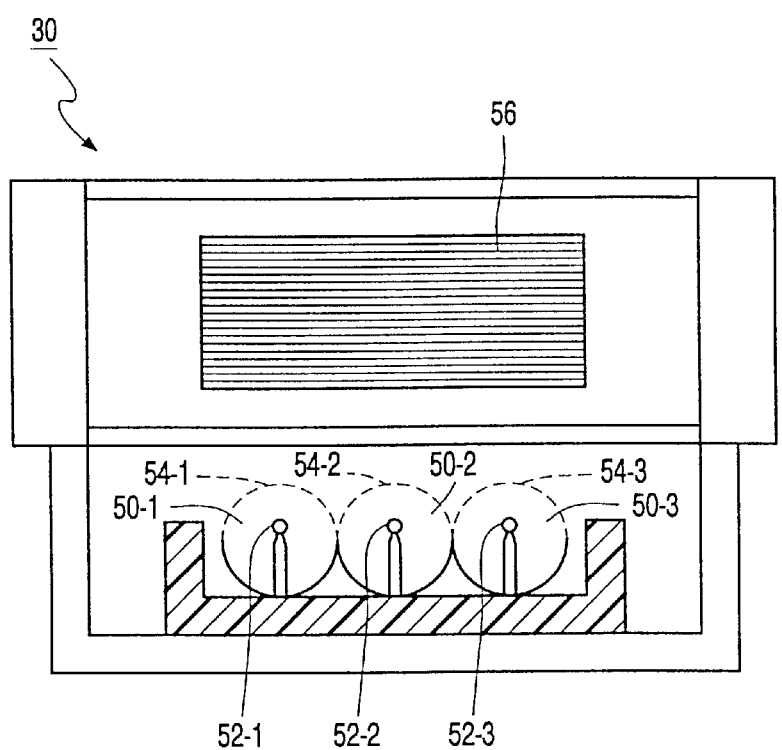
FIG. 3 is a partly sectional front view of a radiation detector according to the invention.

FIG. 3 is a partly sectional front view of the radiation detector 30 according to the invention. The top of this Figure shows the housing of the absorption chamber 46, the front of the collimator 56 also being visible. Below said housing there is shown a cross-section of three avalanche chambers 50-1, 50-2 and 50-3, each of which includes its own counting wire 52-1, 52-2, 52-3 and grid wires 54-1, 54-2, 54-3. The three avalanche chambers 50-i are separated from the absorption chamber 46 by the three sets of grid wires 54-i; these grid wires are not situated completely around the counting wires 52-i. The lower side of the avalanche chambers 50-i, like partitions between these chambers, if desired, may be made of a conductive plate material, because in this configuration no electrons enter the avalanche chambers from the direction of said plate. The grids 54-i are kept in place by a conductive carrier 62. Because of the situation of the three avalanche chambers relative to the absorption chamber as shown, the electrons formed by ionization in the absorption chamber are driven in the direction of the avalanche chambers, so that in comparison with the situation involving only a single avalanche chamber an increased maximum count rate is achieved therein.

Even though the boundary of the avalanche chambers 50-i in the form of the grids is shown to be partly round in FIG. 3, it is very well possible to construct these grids so as to have a squire or rectangular cross-section as is already indicated by way of a part of the grid wires 54-2. When all avalanche chambers have a rectangular or square cross-section, the entire space around the absorption chamber 46 can be filled by means of avalanche chambers which are comparatively small per se, so that all electrons formed by ionization can be detected thereby, without the avalanche chamber (chambers) having to be so large that the duration of the current impulses to be detected would become too long.

What is claimed is:

1. An apparatus for radiation analysis by means of analyzing ionizing radiation, comprising:

a radiation detector for detecting the analyzing radiation, the radiation detector includes:
  a gas-filled absorption chamber for absorbing the radiation to be detected, which absorption chamber is provided with an entrance window which is formed in a wall of the absorption chamber and is transparent to the radiation to be detected, and
  a plurality of counting wires which are arranged in the gas atmosphere, the surface of the entrance window being oriented transversely of the longitudinal direction of the plurality of counting wires,
wherein the radiation detector is also provided with at least two avalanche chambers which adjoin the absorption chamber, are in atmospheric contact therewith and are intended to produce an avalanche of released charged particles, each of said avalanche chambers includes
  a grid which is present in the gas atmosphere and is arranged around at least one of the plurality of counting wires, and wherein at least two of the plurality of counting wires extend substantially parallel to one another.

2. A radiation analysis apparatus as claimed in claim 1, wherein the grid consists of grid wires which extend substantially parallel to at least one of the plurality of counting wires.

3. A radiation analysis apparatus as claimed in claim 1, wherein the avalanche chambers directly adjoin one another.

4. A radiation analysis apparatus as claimed in claim 3, wherein the avalanche chambers and the absorption chamber constitute a contiguous stack.

5. A radiation analysis apparatus as claimed in claim 1, said apparatus being part of an X-ray diffraction apparatus.

6. A radiation analysis apparatus as claimed in claim 1, said apparatus being part of an X-ray fluorescence apparatus.

* * * * *